United States Patent [19]

Svanberg et al.

[11] Patent Number: 4,786,813
[45] Date of Patent: Nov. 22, 1988

[54] FLUORESCENCE IMAGING SYSTEM

[75] Inventors: Sune Svanberg; Sune Montan, both of Lund, Sweden

[73] Assignee: HighTech Network SCI AB, Malmo, Sweden

[21] Appl. No.: 882,975
[22] PCT Filed: Oct. 22, 1985
[86] PCT No.: PCT/SE85/00408
§ 371 Date: Jun. 23, 1986
§ 102(e) Date: Jun. 23, 1986
[87] PCT Pub. No.: WO86/02730
PCT Pub. Date: May 9, 1986

[30] Foreign Application Priority Data

Oct. 22, 1984 [SE] Sweden .................. 8405276

[51] Int. Cl.$^4$ ............................ G01N 21/64
[52] U.S. Cl. .................. 250/461.1; 250/458.1; 250/461.2
[58] Field of Search ............ 250/461.2, 461.1, 459.1, 250/458.1, 578; 350/613, 616

[56] References Cited

U.S. PATENT DOCUMENTS

| | | | |
|---|---|---|---|
| 3,872,312 | 3/1975 | Hirschfeld | 250/461.2 |
| 4,019,060 | 4/1977 | Woodman | 250/461.2 |
| 4,144,452 | 3/1979 | Harte | 250/461.2 |
| 4,272,684 | 6/1981 | Seachman | 250/578 |
| 4,407,008 | 9/1983 | Schmidt et al. | 356/301 |
| 4,573,195 | 2/1986 | de France | 356/39 |

FOREIGN PATENT DOCUMENTS

| | | |
|---|---|---|
| 0040716 | 12/1981 | European Pat. Off. . |
| 0019732 | of 1909 | United Kingdom ........ 350/613 |
| 2126717 | 8/1982 | United Kingdom . |

Primary Examiner—Janice A. Howell
Assistant Examiner—William F. Rauchholz
Attorney, Agent, or Firm—Pollock, Vande Sande & Priddy

[57] ABSTRACT

A fluorescence imaging system. A light source irradiates an object to be viewed. The irradiated object is imaged through a beam-splitting system to form individual displaced images of the object. The displaced images are further filtered in a filter having a frequency passband different from the other filters. The filtered images are imaged on a detector. The same image point of each image is detected and converted into an electrical signal. A circuit means is provided to receive the signals of each common image point, and weight the same. The weighted signal represents an image point pixel. The weighted pixels are displayed as an image of the object having improved contrast.

8 Claims, 2 Drawing Sheets

FLUORESCENCE IMAGING SYSTEM

The invention relates to a fluorescence imaging system of the kind which comprises a light source for irradiating a fluorescent object, a filter for separating fluorescence radiation emitted by the object as a result of irradiation, and detector means for detecting radiation transmitted through the filter, there being arranged between the object and the detector means an imaging optical system having an object image plane located adjacent the detector means.

Systems which fall within this general group are known to the art. Examples of such systems include fluorescence microscopy systems, which are often used in research work. These instruments provide an image produced by fluorescent substances in the object under examination, these substances being either natural substances or fluorescent dyes.

Many solid and liquid substances emit fluorescence radiation when irradiated with ultraviolet light, which radiation may fall within wide wavelength bands of but low structural profiles, and hence identification on the basis of spectroscopy is difficult. However, in conventional fluorescence analysis, e.g. in fluorescence microscopy, there is normally incorporated in the optical system a filter for a selected wavelength band. In the case of slightly complex situations, observations are often disturbed by contributions emanating from the many different compounds present in the sample under examination.

An object of the present invention is to provide a fluorescence imaging system with which fluorescence reproduction can be achieved with improved significance, by eliminating irrelevant fluorescence radiation, even when a certain spectral overlap prevails between the fluorescence radiation desired to be imaged and the disturbing fluorescence radiation.

This object is achieved in accordance with the invention by providing a fluorescence imaging system of the kind described in the introduction with a beam-splitting system arranged to split the fluorescence radiation passing through the optical system into at least three parts, each of which parts forms a respective image of the object, which image is displaced in the image plane relative to the other imges and falls on a respective detector-area in the detector means, the various parts of the beam being led through a respective filter, each filter being of mutually different frequency pass-band, there being obtained thereby an image of the object within each respective wavelength region in the form of a plurality of image points for each, the detector means being arranged to produce a respective signal for each of said points, means being provided for performing a mathematical and/or logic operation for signals deriving from each image point corresponding to one and the same point on the object, so as to obtain a weighted signal value and to produce an image of the object from the weighted signal values of the various points on the object.

The imaging system should be achromatic. Consequently, in accordance with a preferred embodiment, the beam splitting system comprises a mirror which is incorporated in the optical system and divided into a plurality of parts, each positioned at a mutually different angle to reproduce the object on different parts of the detector plane. Both planar and spherical mirrors can be used, as can also other beam-splitting systems of a known kind.

The filters used should be filter constructions capable of producing well defined band-pass curves, and particular benefit is obtained in this respect when interference filters are used.

In order to understand the difference between ordinary fluorescence imaging and that of the invention, it is suitable to consider the spectrum illustrated in FIG. 2a. Tumor cells have the ability to retain the substance hematoporphyrine-derivative (HPD). The characteristic fluorescence spectrum for this substance lies within the range of 610–700 nm, which corresponds to the peaks referenced A and C in the figure. Other substances in the cells, however, fluoresce much more strongly, and produce a broader band spectrum, such as shown at B in FIG. 2a. The part of the curve shown in a broken line illustrates the sloping background of irrelevant fluorescence radiation on which the band structures A and C from HPD are superimposed. It is possible by means of the present invention to eliminate, to a very large extent, this source of irrelevant disturbance which destroys the image contrast when using only, as in conventional fluorescence microscopy, a filter which is adapted to the relevant radiation.

The invention will now be described in more detail with reference to the drawing.

DESCRIPTION OF THE PREFERRED EMBODIMENT

Figure 1:
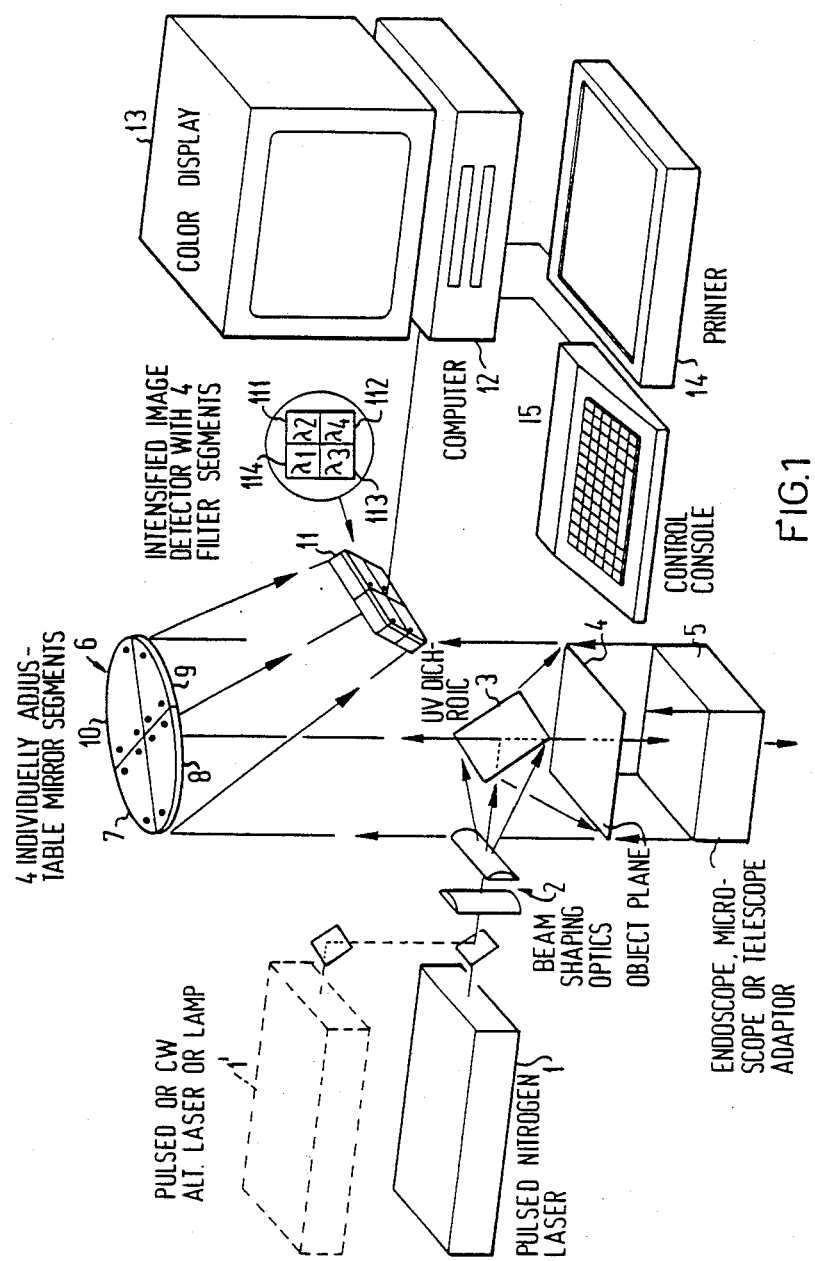
FIG. 1 is a schematic diagram of a fluorescence imaging system constructed in accordance with the principles of the invention.

FIG. 1 illustrates the principal construction of a fluorescence imaging system according to the invention. The light source used to produce ultraviolet radiation is either a pulsed nitrogen laser 1 or a pulsed or continuous light source 1'. In one preferred embodiment there is used a pulsed $N_2$-laser of the kind which emits light radiation at 337 nm in 5 ns pulses at a repetition frequency of 10–100 Hz. The PRA Model LN 250 is an example of such a laser. When very high power is required, an XeCl excimer laser can be used. A Lambda Physic Model 102 E is an example of such a laser. In some cases a mercury or xenon lamp (Oriel, Osram), pulsed or continuous, provided with a filter, will suffice. The object is irradiated with the aid of some form of collimator device, so that the object under examination is properly illuminated. This can be achieved with the aid of quartz cylinder lenses 2 (Esco Products). To this end there is used a dichroic UV-mirror 3 (from Balzers) which entirely reflects ultraviolet radiation, but is highly transparent to fluorescence radiation lying in the visible spectrum and close to the IR-range. This mirror should be large enough to cover the whole of the aperture of the optical system 5, which may have the form of an endoscope, a microscope or a telescope. The optical system 5 has an object plane at 4. In the simplest version of the system, the object is placed in this object plane. The object plane is imaged on a detector 11 by means of a spherical, surface-aluminized mirror 6. Such mirrors can be obtained from the company Bernard Halle. Such a mirror is achromatic of function. The mirror 6 is concave and divided into four parts 7-10, each of which is also concave and individually adjustable, such that the four mirror parts per se can be caused to reproduce the object plane 4 in four mutually different fields $\lambda_1, \lambda_2, \lambda_3, \lambda_4$. In the illustrated embodiment the detector 11 is a matrix diode detector from Reticon, incorporating, for example, 512×512 light sensitive detector elements. Alternatively, there may be used a vidicon tube, for example. Normally an image intensifier (VARO) is placed in front of the detector and activated synchronously with the pulses arriving from the pulsated light source, thereby to provide brighter and sharper images while suppressing ambient light and improving the signal/noise ratio. Located in front of the detector system are four square filters 111-114, each of which allows light of a respective wavelength band to pass through. These filters are preferably interference filters, although color filters may also be used in certain cases. Interference filters can be obtained from either of the companies Oriel or Corion.

Subsequent to integration in the detector, the detector signals are transmitted to a computer system 12 in which the signals are processed. The signals are accumulated over a sufficiently long period of time to yield a good signal to noise ratio. When deemed necessary, for example because of distortion in the lens system, a coordinate rectification can be effected initially.

For each image point there is thus obtained from the detector 11 four different signals, which signals are processed mathematically in a manner hereinafter described, and the result can then be viewed on a screen 13, or can be permanently recorded with the aid of a writer 14. The computer system 12 includes a terminal 15, with which the manner in which the image is processed can be controlled.

As will be seen from FIG. 1, the most important characteristic of the invention resides in the division of the fluorescence radiation from the optical system 5 and the intermediate-image plane 4 into a number of images which through filtration represent the two-dimensional reproduction of the object in a respective fluorescence wavelength band.

Figure 2A:
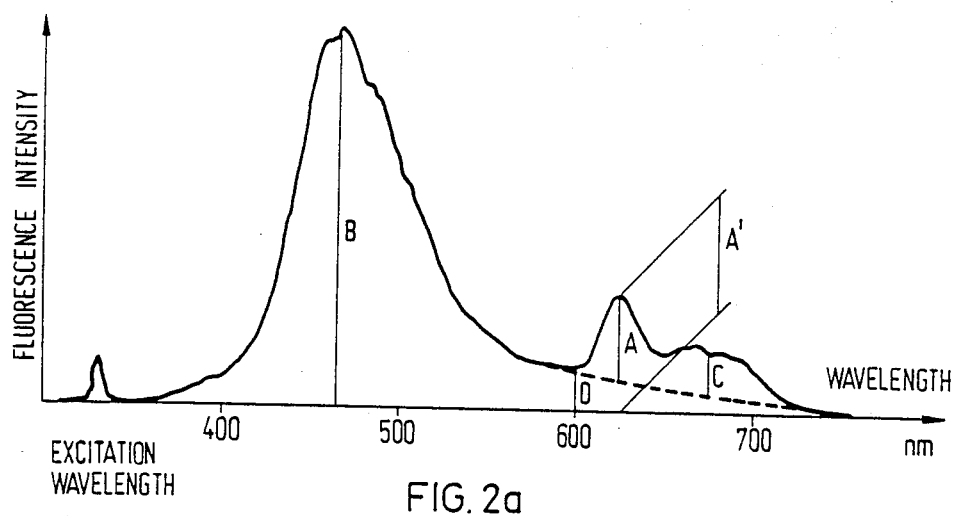
FIG. 2a, already commented upon, illustrates a spectrum of fluorescence radiation emitted from a cancer cell preparation labelled with HPD.

An illustrative example of one application of the imaging system will now be described with reference to FIG. 2a, which illustrates a typical fluorescence spectrum of a cancer tumor which selectively retains HPD-molecules. The characteristic signature of this substance lies in the spectral range of 610-700 nm. The fluorescence B emanating from the tissues themselves and constituting background can be much stronger than appears from the figure. An optimized contrast function $F_c$ can be $$F_c = \frac{A' - kD}{B}$$

where A', D and B are the intensities apparent from the figure, while k is a constant. The signal levels of A', D and B are detected through interference filters centered at 630, 600 and 480 nm respectively. The constant k is calculated from the sloping background curve determined through the signal levels at B and D. It is possible by means of this procedure to lift-off the red HPD peak and remove it from the background. By dividing by the signal B a dimensionless magnitude can be obtained. This affords an advantage, since the dimensionless magnitude is immune to geometric artefacts resulting from the topography of the surface, so that only changes in the molecular composition will be manifested. Irregularities in illumination (spacial and temporal variations) also become of but small significance. In addition contrast is further greatly enhanced, owing to the fact that, as established experimentally, the blue (B) fluorescence tends to decrease in tumor tissue, such that in the aforegiven expression the numerator increases at the same time as the denominator decreases at the precise location of the tumor. In some cases, for example when the tumor is heavily stained with blood, the fluorescence is greatly decreased, due to attenuation by absorption. The ratio A/B, however, remains substantially unchanged and discloses the presence of the tumor. This is in strong contrast to the erroneous results obtained when practising the methods known hitherto, in which only the total red fluorescence is measured. Some normal tissues (for example the skin of rats), exhibit a normal red fluorescence peak at about 630 nm, which can be confused with HPD. In these cases, however, the ratio A/C (see FIG. 2a) differs from the ratio characteristic for HPD. By using the fourth image in the system for signal C, it is possible to form in the computer system the ratio, or quotient, A/C, and to use this ratio as a criterion for accepting or rejecting $F_c$-data obtained from the other three channels. By setting suitable discrimination thresholds in this regard, it is possible hereby to display only those parts of the tissue that have typical characteristics of cancer tissue. The same type of contrast function (X-Y)/Z can be employed in other cases in which a reasonably characteristic, sharp peak is found. One example in this regard relates to vegetation, in which chlorophyll-a presents a sharp peak at 685 nm.

Detection of cancer tissue with the aid of HPD is a particularly interesting example of the use to which the present invention can be put, since the invention can be applied for early detection of otherwise not-readily diagnosed malignant tumors in the lungs, the bladder, the esophagus, the stomach etc., even in the presence of powerful background fluorescence. Normal endoscopic techniques can then be applied together with the invention. The size of a tumor can be evaluated and post-operative checks carried out, to ensure that sufficient tissue has been removed. One advantage afforded by the significant increase in contrast achieved by means of the invention as compared with conventional imaging in red fluorescence is that less HPD is required. An advantage thereby obtained is the decrease in the photosensibilization of the patient. With the techniques at present applied, the patient must avoid strong daylight for one month from the time of the examination. Since the dosage can be reduced when applying the present invention, this safety margin can be radically decreased, such as to render the method feasible for use in monitoring certain risk groups of the population. It is also likely that small changes in tumor-cell fluorescence emissions not capable of being observed with earlier techniques and occurring naturally so to speak, can be used for future tumor detection, therewith obviating the need of injecting foreign substances intravenously into the body.

The invention can also be applied industrially. For example, the invention has been applied experimentally to test the surface cleanliness of metal plate prior to painting the same, these tests enabling the contaminated plate to be automatically discarded from the system and returned for further cleansing. The invention can also be applied in other fields. For example, fluorescence methodology is applied in forensic techniques for rendering visible fingerprints, detecting forgeries etc. These methods can be made more effective by means of the present invention, enabling for example extremely faint fingerprints to be made visible, even when found on material from which fingerprints cannot readily be reproduced or on material previously considered impossible to read in this respect.

Monitoring can be effected in a similar manner in respect to coatings of anti-corrosion greases, oils and like substances, such as paint layers and adhesive layers, or when studying corrosion. In this regard, in order to provide a suitable field of view, the optical system may include a telescope having an adapted viewing angle. The invention can also be employed in the inspection of printed circuits and the like. In the case of advanced inspection modes, the observed contrast functional image can be compared with a standard image previously registered in a computer memory, the extent to which the comparison conforms deciding whether the examined object is accepted or rejected. When the resolution is sufficiently high, one of the image channels can be used for conventional imaging, for example in reflected light, so as to obtain a mixture of measurements in fluorescence and normal light. In some process control operations, for example monitoring of chemical processes, non-imaging point measurements may be sufficient, thereby enabling the use of a simplified single-point system operating with the same beam-splitting and filter technique, but utilizing photomultipliers as detectors.

Many valuable minerals fluoresce, particularly the tungsten mineral scheelite. The contrast enhancing arrangement according to the invention enables rock samples to be examined for specific mineral crystals. For example, a vehicle-mounted instrument provided with a telescope adapter can be used to inspect rock walls or the like in quarries and road cuttings.

When the instrument is utilized in a telescope, aerial surveys can be made with the purpose, for example, of examining oil slicks or the growth of algal blooms on the surface of water. In this case there is preferably used a linear detector array, in which the four filters are placed in a row, and the movement of the airborne craft carrying the instrument is utilized to produce successive image lines, approximately in the same manner as that effected in SLAR-systems (Side Looking Airborne Radar). The excitation light source then simultaneously illuminates a line on the surface, therewith inducing a line of fluorescence light. The simultaneous multi-colour detection eliminates those problems associated with the rapid movement to which the instrument is subjected and which causes difficulties when applying conventional scanning techniques. Hydrospheric dynamics can also be studies, using fluorescence dyes such as Rhodamine B. The method can also be applied in the study of stress in vegetation due to drought, disease and insect attack.

Figure 2B:
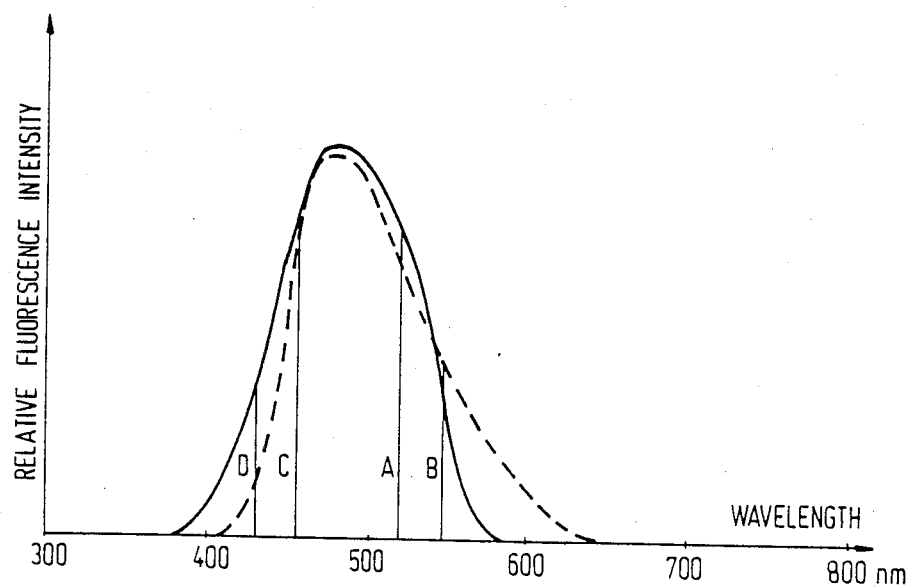
FIG. 2b is an illustrative reproduction of two, not-readily separated fluorescence spectra.

As beforementioned, the majority of fluorescence spectra have but low characteristic structural profiles, rendering it difficult to distinguish between substances when applying conventional techniques. FIG. 2b illustrates two examples of substantially structure-free spectra. Although the illustrated spectra are highly similar, small changes in slope can be used for discrimination purposes. In this case it is possible to form two "derivatives" at suitably selected wavelengths, and to calculate the ratio of the derivatives (constituting a dimensionless quantity which, in accordance with the aforegoing, is free from many undesirable disturbances). A suitable contrast function can then be $$F_c = \frac{A - B}{C - D}$$

Such a contrast function results in the emphasis of parts of the full-line spectral band curve in FIG. 2b to the detriment of the broken-line curve, since the full-line curve is steeper between A and B and flatter between C and D than the broken-line curve. In view of the fact that interference filters of practically any desired frequency and also of practically any desired band width can be readily obtained from the manufacturers, the invention can be applied with great freedom and within a large number of fields.

The invention can also be applied in conjunction with known pseudo-color methods, since with separate, arbitrarily selected colours or dyes it is possible to reproduce on a video-monitor both differences in wavelength at different image points and differences in the intensity or the value of the various, detected or estimated variables for each image point.

We claim:

1. A fluorescence imaging system comprising:
   a light source for irradiating an object to be viewed;
   a beam-splitting system for forming individual displaced images of said irradiated object;
   a plurality of wavelength filters disposed in the path of said individual images, said filter selected to have different passband frequencies, such that said images are filtered differently;
   a detector for receiving said individual displaced images which pass through said filters, said detector providing a plurality of signals representing the same image point of each of said displaced images; and,
   circuit means connected to receive said signals representing the same image point for each of said displaced images, said circuit means generating a weighted signal value of said individual signals, such that a single image signal is produced for each image point of an image of said object.

2. A fluorescence imaging system according to claim 1, wherein the beam-splitting system comprises a mirror, which is incorporated in the optical system and divided into several parts, said parts being mutually angled at a position to image the object on different parts of the plane of said detector.

3. A fluorescence imaging system according to claim 2, wherein the divided mirror is a concave mirror, with each part thereof also being concave.

4. A fluorescence imaging system according to claim 1, wherein the filters are interference filters.

5. A fluorescence imaging system according to claim 1, wherein the weighted signal value is dimensionless and unrelated to absolute values of signal intensity.

6. A fluorescence imaging system according to claim 1, wherein an optical imaging system which images the object in an object plane, is arranged, in the light path, between the beam-splitting system and said object.

7. A fluorescence imaging system according to claim 6, wherein the light source includes a second beam-splitting system, to irradiate the object via the optical imaging system.

8. A fluorescence imaging system according to claim 1, characterized in that the light source is pulsatable laser; and in that means are provided for activating the detector means at each laser pulse.

* * * * *